United States Patent
Fuchigami et al.

(10) Patent No.: US 9,547,900 B2
(45) Date of Patent: Jan. 17, 2017

(54) IMAGE PROCESSING APPARATUS, X-RAY DIAGNOSIS APPARATUS, AND REGISTRATION METHOD

(71) Applicant: Toshiba Medical Systems Corporation, Otawara-shi (JP)

(72) Inventors: Ko Fuchigami, Otawara (JP); Takuya Sakaguchi, Utsunomiya (JP); Shinichi Hashimoto, Otawara (JP); Hiroyuki Ohuchi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 13 days.

(21) Appl. No.: 14/663,232

(22) Filed: Mar. 19, 2015

(65) Prior Publication Data
US 2015/0193931 A1 Jul. 9, 2015

Related U.S. Application Data

(63) Continuation of application No. PCT/JP2013/075559, filed on Sep. 20, 2013.

(30) Foreign Application Priority Data

Sep. 20, 2012 (JP) .................................. 2012-206945

(51) Int. Cl.
| | |
|---|---|
| G06K 9/00 | (2006.01) |
| G06T 7/00 | (2006.01) |
| A61B 6/12 | (2006.01) |
| A61B 6/00 | (2006.01) |

(Continued)

(52) U.S. Cl.
CPC ............... *G06T 7/0024* (2013.01); *A61B 6/12* (2013.01); *A61B 6/4417* (2013.01);
(Continued)

(58) Field of Classification Search
None
See application file for complete search history.

(56) References Cited

U.S. PATENT DOCUMENTS

8,308,644 B2 * 11/2012 McMorrow ............... A61B 8/08
600/437
2001/0029334 A1 10/2001 Graumann et al.
(Continued)

FOREIGN PATENT DOCUMENTS

| JP | 10-137238 A | 5/1998 |
|---|---|---|
| JP | 2001-218765 A | 8/2001 |

(Continued)

OTHER PUBLICATIONS

International Search Report issued Oct. 29, 2013 in International Application No. PCT/JP2013/075559 filed Sep. 20, 2013(with English translation).

(Continued)

*Primary Examiner* — Hadi Akhavannik
(74) *Attorney, Agent, or Firm* — Oblon, McClelland, Maier & Neustadt, L.L.P.

(57) ABSTRACT

An image processing apparatus according to an embodiment includes an acquiring unit and a determination unit. The acquiring unit acquires information of a relative position between a radiographic space where a subject is radiographed by an X-ray diagnosis apparatus and a scanning space where the subject is scanned by an ultrasound probe. The determination unit determines a position almost the same as the position scanned by the ultrasound probe in the radiographic space, according to the information of the relative position acquired by the acquiring unit. The acquiring unit acquires the information of the relative position based on an X-ray image radiographed by the X-ray diagnosis apparatus.

10 Claims, 10 Drawing Sheets

(51) Int. Cl.
*A61B 8/08* (2006.01)
*A61B 8/00* (2006.01)

(52) U.S. Cl.
CPC .......... *A61B 6/5247* (2013.01); *A61B 8/0883* (2013.01); *A61B 8/4416* (2013.01); *A61B 8/463* (2013.01); *A61B 8/466* (2013.01); *A61B 8/5207* (2013.01); *A61B 8/5261* (2013.01); *G06T 7/0012* (2013.01); *A61B 6/4441* (2013.01); *A61B 6/481* (2013.01); *A61B 8/4254* (2013.01); *G06T 2207/10116* (2013.01); *G06T 2207/10132* (2013.01); *G06T 2207/30004* (2013.01)

(56) References Cited

U.S. PATENT DOCUMENTS

| | | |
|---|---|---|
| 2002/0049375 A1 | 4/2002 | Strommer et al. |
| 2002/0090058 A1 | 7/2002 | Yasuda et al. |
| 2008/0234570 A1 | 9/2008 | Gerard et al. |
| 2009/0043200 A1 | 2/2009 | Abe |
| 2012/0245458 A1 | 9/2012 | Gogin et al. |

FOREIGN PATENT DOCUMENTS

| | | |
|---|---|---|
| JP | 2002-136507 A | 5/2002 |
| JP | 2004-533863 A | 11/2004 |
| JP | 2007-526066 A | 9/2007 |
| JP | 2009-39429 A | 2/2009 |
| JP | 2010-162058 A | 7/2010 |
| JP | 2012-152519 A | 8/2012 |
| WO | WO 2011-070477 A1 | 6/2011 |

OTHER PUBLICATIONS

Written Opinion issued Oct. 29, 2013 in International Application No. PCT/JP2013/075559 filed Sep. 20, 2013.

* cited by examiner

POSITION OF TIP OF ULTRASOUND PROBE (x1, y1, z1)

X-RAY COORDINATE SYSTEM

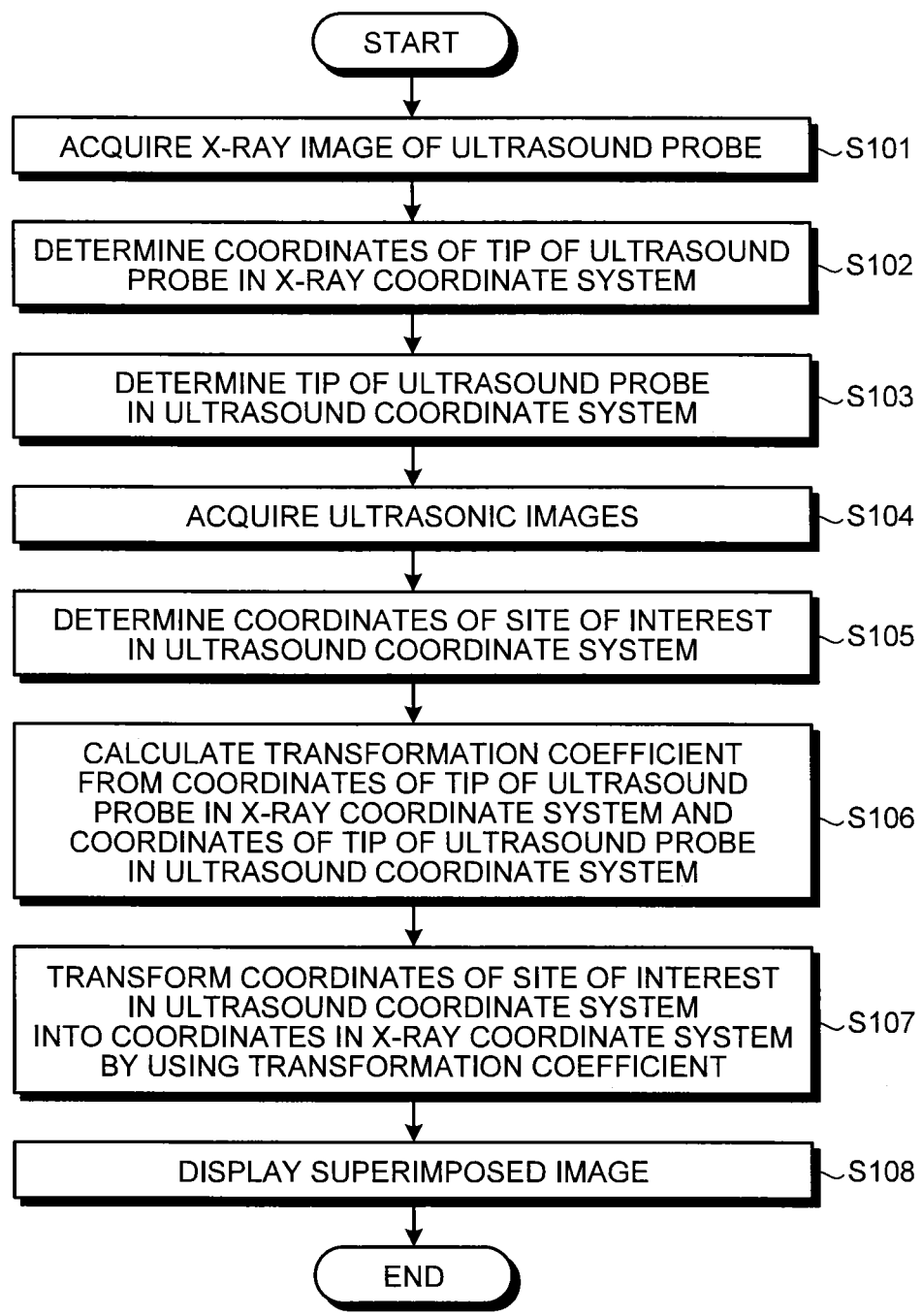

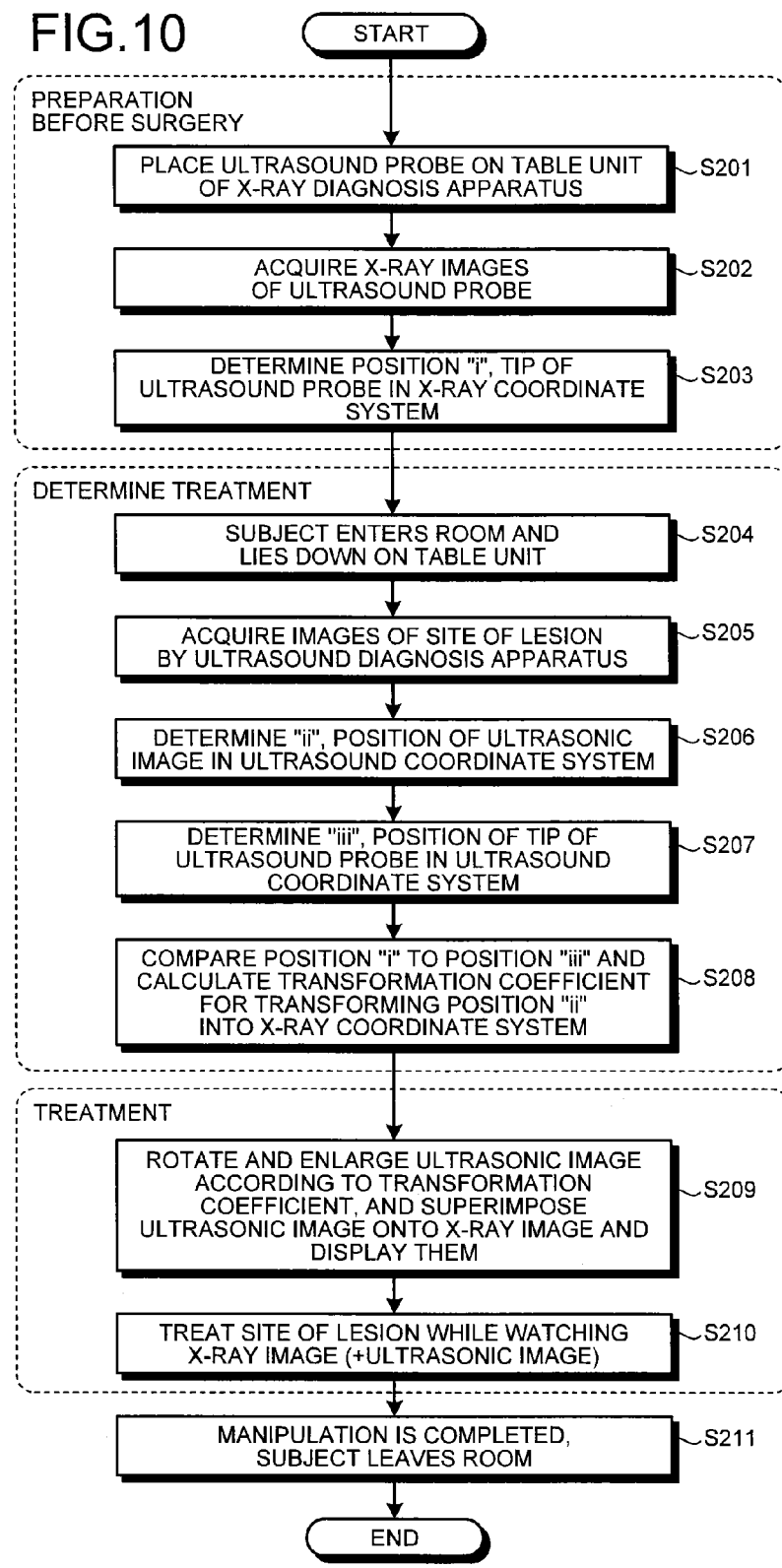

IMAGE PROCESSING APPARATUS, X-RAY DIAGNOSIS APPARATUS, AND REGISTRATION METHOD

CROSS-REFERENCE TO RELATED APPLICATIONS

This application is a continuation of International Application No. PCT/JP2013/075559, filed on Sep. 20, 2013 which claims the benefit of priority of the prior Japanese Patent Application No. 2012-206945, filed on Sep. 20, 2012, the entire contents of which are incorporated herein by reference.

FIELD

Embodiments described herein relate generally to an image processing apparatus, an X-ray diagnosis apparatus, and a registration method.

BACKGROUND

Conventionally, the cardiac resynchronization therapy (CRT) has been known as an example of heart failure treatment. This therapy is used for treatment of a disease in which abnormality of the impulse conduction system of the heart leads to a wrong timing of motion of the cardiac muscle surrounding a ventricle, so that core-walls of the right and left ventricles do not move at the same time, and the ventricles do not contract at the correct timing, thus causing insufficient cardiac output of the blood, for example.

In the CRT, an electrode is placed in the part where the heart hardly moves (the site of latest activation) so that the ventricles of the heart contract in a synchronized manner. Specifically, in the CRT, the site of latest activation is determined through strain analysis by using an ultrasound diagnosis apparatus, and the electrode is placed on the closest vein to the site of latest activation with reference to the X-ray image radiographed by an X-ray diagnosis apparatus.

The electrode placed as described above applies stimuli electric potential at a proper timing, whereby the cardiac muscle contracts at a proper timing and controls the motion of the ventricles. In the conventional technology, however, correct positional information of the site of latest activation in an X-ray image can be hardly obtained.

BRIEF DESCRIPTION OF THE DRAWINGS

FIG. 9 is a flowchart illustrating procedures for processing performed by the image processing apparatus according to the first embodiment; and FIG. 10 is a flowchart illustrating procedures of a surgeon using the image processing apparatus according to the first embodiment.

DETAILED DESCRIPTION

According to embodiment, an image processing apparatus includes an acquiring unit and a determination unit. The acquiring unit that acquires information of a relative position between a radiographic space where a subject is radiographed by an X-ray diagnosis apparatus and a scanning space where the subject is scanned by an ultrasound probe. The determination unit that determines a position almost the same as the position scanned by the ultrasound probe in the radiographic space, according to the information of the relative position acquired by the acquiring unit. The acquiring unit acquires the information of the relative position based on an X-ray image radiographed by the X-ray diagnosis apparatus.

Figure 1:
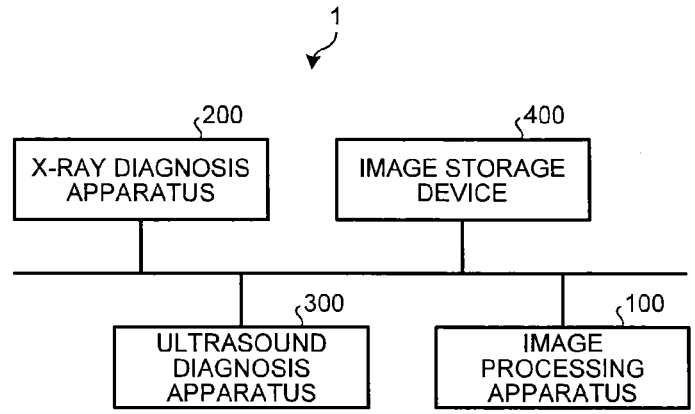
FIG. 1 is a diagram illustrating an example of the configuration of an image processing system according to a first embodiment.

Hereinafter, embodiments of an image processing apparatus according to the present application are described in detail below. In a first embodiment, an image processing system including an image processing apparatus according to the present application is described as an example. FIG. 1 is a diagram illustrating an example of the configuration of an image processing system according to a first embodiment.

As illustrated in FIG. 1, an image processing system 1 according to the first embodiment includes an image processing apparatus 100, an X-ray diagnosis apparatus 200, an ultrasound diagnosis apparatus 300, and an image storage device 400. The apparatuses illustrated in FIG. 1 are in a communicable state directly or indirectly to each other through a local area network (LAN) provided in a hospital, for example. When a picture archiving and communication system (PACS) is implemented in the image processing system 1, the apparatuses transmit and receive medical images to and from each other according to the digital imaging and communications in medicine (DICOM) standard.

In the image processing system 1, the X-ray diagnosis apparatus 200 acquires X-ray images according to the operations of the engineer (operator) of the apparatus and the ultrasound diagnosis apparatus 300 acquires ultrasonic images according to the operations of the engineer (operator) of the apparatus. The image processing apparatus 100 then displays the ultrasonic image appropriately registered with the X-ray image. This enables a doctor to place an electrode on a placing position planned using the ultrasound diagnosis apparatus in a precise manner while performing the cardiac resynchronization therapy (CRT).

The image storage device 400 is a database that stores medical images. Specifically, the image storage device 400 according to the first embodiment records X-ray images transmitted from the X-ray diagnosis apparatus 200 and ultrasonic images transmitted from the ultrasound diagnosis apparatus 300 in a storage unit and stores the images therein. That is, the image processing apparatus 100 according to the first embodiment may receive the image data directly from the X-ray diagnosis apparatus 200 or the ultrasound diagnosis apparatus 300, and may acquire the images temporarily stored in the image storage device 400.

Figure 2:
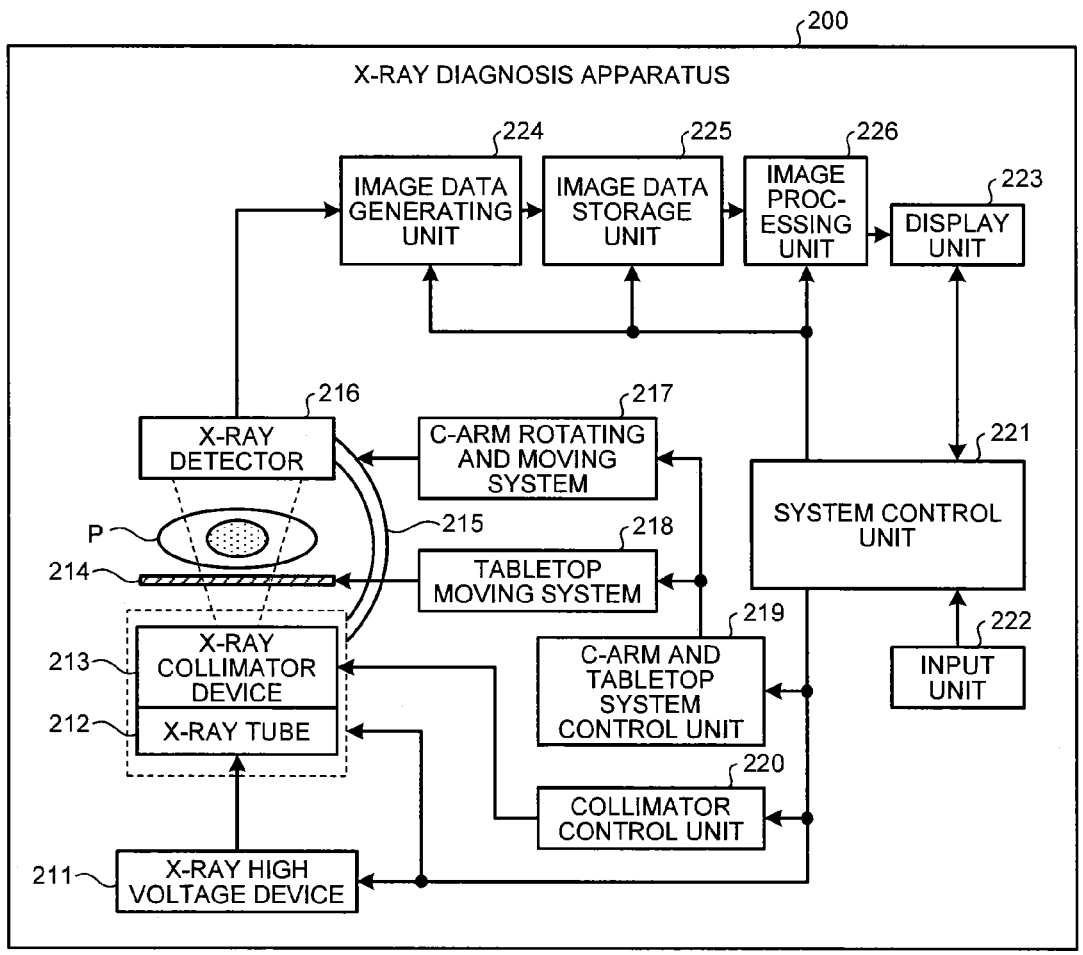
FIG. 2 is a diagram illustrating an example of the configuration of an X-ray diagnosis apparatus according to the first embodiment.

Firstly, the following describes the configuration of the X-ray diagnosis apparatus 200 according to the first embodiment. FIG. 2 is a diagram illustrating an example of the configuration of the X-ray diagnosis apparatus 200 according to the first embodiment. As illustrated in FIG. 2, the X-ray diagnosis apparatus 200 according to the first embodiment includes an X-ray high voltage device 211, an X-ray tube 212, an X-ray collimator device 213, a tabletop 214, a C-arm 215, and an X-ray detector 216. The X-ray diagnosis apparatus 200 according to the first embodiment also includes a C-arm rotating and moving system 217, a tabletop moving system 218, a C-arm and tabletop system control unit 219, a collimator control unit 220, a system control unit 221, an input unit 222, and a display unit 223. Furthermore, the X-ray diagnosis apparatus 200 according to the first embodiment includes an image data generating unit 224, an image data storage unit 225, and an image processing unit 226.

The X-ray high voltage device 211 generates a high voltage under the control of the system control unit 221 and supplies the generated high voltage to the X-ray tube 212. The X-ray tube 212 generates X-rays using the high voltage supplied from the X-ray high voltage device 211.

The X-ray collimator device 213 narrows down the X-rays generated by the X-ray tube 212 under the control of the collimator control unit 220 so that the region of interest of a subject P is selectively irradiated with the X-rays. For example, the X-ray collimator device 213 includes four slidable collimator blades. The X-ray collimator device 213 slides the collimator blades under the control of the collimator control unit 220, thereby narrowing down the X-rays generated by the X-ray tube 212 so that the subject P is irradiated with the X-rays. The tabletop 214 is a bed for mounting the subject P and disposed on a not-illustrated table unit. The subject P is not included in the X-ray diagnosis apparatus 200.

The X-ray detector 216 detects the X-rays transmitted through the subject P. For example, the X-ray detector 216 includes detecting elements arranged in a matrix shape. Each of the detecting elements converts the X-ray transmitted through the subject P into the electrical signals, accumulates them, and transmits the accumulated electrical signals to the image data generating unit 224.

The C-arm 215 retains the X-ray tube 212, the X-ray collimator device 213, and the X-ray detector 216. The X-ray tube 212 and the X-ray collimator device 213 are disposed on an opposite side of the X-ray detector 216 across the subject P and supported by the C-arm 215.

The C-arm rotating and moving system 217 is a system for rotating and moving the C-arm 215. The tabletop moving system 218 is a system for moving the tabletop 214. The C-arm and tabletop system control unit 219 controls the C-arm rotating and moving system 217 and the tabletop moving system 218 under the control of the system control unit 221, thereby adjusting the rotation and movement of the C-arm 215, and the movement of the tabletop 214. The collimator control unit 220 adjusts the degree of opening of the collimator blades included in the X-ray collimator device 213 under the control of the system control unit 221, thereby controlling the radiation range of the X-rays with which the subject P is irradiated.

The image data generating unit 224 generates image data using the electrical signals converted by the X-ray detector 216 from the X-rays, and stores the generated image data in the image data storage unit 225. For example, the image data generating unit 224 performs various types of processing such as current-voltage conversion, analog-digital (A/D) conversion, and parallel-serial conversion on the electrical signals received from the X-ray detector 216, thereby generating the image data.

The image data storage unit 225 stores therein the image data generated by the image data generating unit 224. The image processing unit 226 performs various types of image processing on the image data stored in the image data storage unit 225. Details of the image processing performed by the image processing unit 226 are described later.

The input unit 222 receives various types of instructions from an operator such as a doctor and an engineer who operates the X-ray diagnosis apparatus 200. For example, the input unit 222 includes a mouse, a keyboard, a button, a trackball, and a joystick, for example. The input unit 222 transfers the instruction received from the operator to the system control unit 221. For example, the input unit 222 receives an instruction for turning the power of the X-ray diagnosis apparatus 200 ON.

The display unit 223 displays a graphical user interface (GUI) for receiving instructions by the operator, and image data stored in the image data storage unit 225. For example, the display unit 223 includes a monitor. The display unit 223 may include a plurality of monitors.

The system control unit 221 controls the overall operations of the X-ray diagnosis apparatus 200. For example, the system control unit 221 controls the X-ray high voltage device 211 according to the operator's instruction forwarded from the input unit 222 to adjust the voltage supplied to the X-ray tube 212, thereby controlling the amount of X-rays or turning ON and OFF of X-rays with which the subject P is irradiated. For another example, the system control unit 221 controls the C-arm and tabletop system control unit 219 according to the operator's instruction to adjust the rotation and movement of the C-arm 215, and the movement of the tabletop 214. For still another example, the system control unit 221 controls the collimator control unit 220 according to the operator's instruction by an operator to adjust the degree of opening of the collimator blades included in the X-ray collimator device 213, thereby controlling the radiation range of the X-rays with which the subject P is irradiated.

The system control unit 221 controls image data generating processing performed by the image data generating unit 224, image processing performed by the image processing unit 226, or analysis processing according to the operator's instruction by an operator. The system control unit 221 performs control for displaying on the monitor or monitors of the display unit 223 a graphical user interface (GUI) for receiving instructions by the operator and images stored in the image data storage unit 225.

Figure 3:
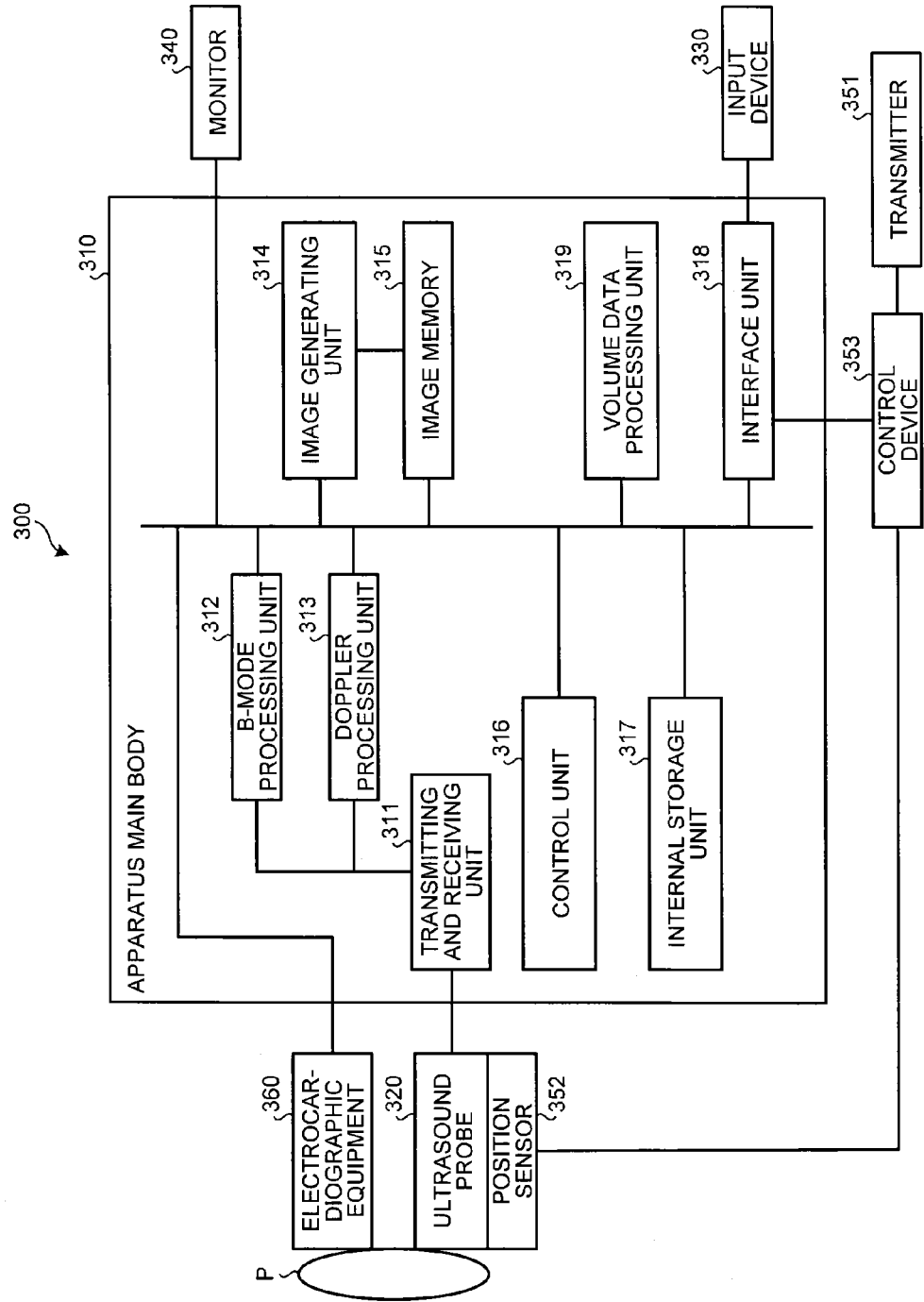
FIG. 3 is a diagram illustrating an example of the configuration of an ultrasound diagnosis apparatus according to the first embodiment.

The following describes the configuration of the ultrasound diagnosis apparatus according to the first embodiment with reference to FIG. 3. FIG. 3 is a diagram for explaining the configuration of the ultrasound diagnosis apparatus 300 according to the first embodiment. As illustrated in FIG. 3, the ultrasound diagnosis apparatus 300 according to the first embodiment includes an apparatus main body 310, an ultrasound probe 320, an input device 330, a monitor 340, a transmitter 351, a position sensor 352, a control device 353, and electrocardiographic equipment 360.

The ultrasound probe 320 includes a plurality of piezoelectric transducer elements that generate ultrasound based on driving signals supplied from a transmitting and receiving unit 311 included in the apparatus main body 310, which will be described later. In addition, the ultrasound probe 320 receives a reflected wave from the subject P and converts it into electrical signals. The ultrasound probe 320 includes a matching layer provided for the piezoelectric transducer elements, and a backing material that prevents the ultrasound of piezoelectric transducer elements from being transmitted backward. For example, the ultrasound probe 320 is a sector ultrasound probe, a linear ultrasound probe, or a convex ultrasound probe.

When the ultrasonic wave is transmitted from the ultrasound probe 320 to the subject P, the transmitted ultrasonic wave is sequentially reflected on discontinuity surfaces of acoustic impedance in internal body tissues of the subject P, and received by a plurality of piezoelectric transducer elements included in the ultrasound probe 320 as reflected wave signals. The amplitude of the received reflected wave signals depends on the difference of the acoustic impedance on the surfaces of discontinuity where the ultrasonic wave is reflected. It should be noted that the reflected wave signals obtained when the transmitted ultrasound pulse is reflected on the surfaces of a moving bloodstream or a moving cardiac wall (i.e., moving object) receives frequency shift depending on the velocity component with respect to the ultrasound transmission direction of the moving object due to the Doppler effect.

In the present embodiment, the subject P is scanned in three dimensions by the ultrasound probe 320. The ultrasound probe 320 may mechanically swing and move a plurality of piezoelectric transducer elements of a one-dimensional ultrasound probe. The ultrasound probe 320 may be a two-dimensional ultrasound probe having a plurality of piezoelectric transducer elements arranged in two dimensions in a matrix shape.

The input device 330 includes a trackball, a switch, a button, and a touch command screen and receives various types of setting demands from an operator of the ultrasound diagnosis apparatus 300. The input device 330 then transfers the received various types of setting demands forward to the apparatus main body 310.

The monitor 340 displays a graphical user interface (GUI) used for inputting various types of setting demands by the operator of the ultrasound diagnosis apparatus 300 using the input device 330. The monitor 340 also displays side by side an ultrasonic image and an X-ray computed tomography (CT) image generated in the apparatus main body 310.

The transmitter 351 transmits a reference signal. Specifically, the transmitter 351 is disposed in an arbitrary position and forms a magnetic field outward with itself as the center of the magnetic field. The position sensor 352 receives the reference signal, thereby acquiring the positional information in the three-dimensional space. Specifically, the position sensor 352 is mounted on the surface of the ultrasound probe 320 and detects the three-dimensional magnetic field formed by the transmitter 351. The position sensor 352 then converts information of the detected magnetic field into signals and outputs the signals to the control device 353. The electrocardiographic equipment 360 is connected to the apparatus main body 310 and acquires an electrocardiogram (ECG) of the subject P on which ultrasound scanning is performed. The electrocardiographic equipment 360 transmits the acquired electrocardiogram to the apparatus main body 310.

The control device 353 calculates the coordinates and the orientation of the position sensor 352 in the space having the transmitter 351 as its origin based on the signals received from the position sensor 352. The control device 353 then outputs the calculated coordinates and orientation to a control unit 316 of the apparatus main body 310. It should be noted that the diagnosis of the subject P is performed in the magnetic field area where the position sensor 352 mounted on the ultrasound probe 320 can precisely detect the magnetic field of the transmitter 351. In the embodiment, a magnetic sensor is used as a sensor that acquires positional information, however, the embodiment is not limited to this example. An infrared sensor, an optical sensor, or a camera may be used instead of the magnetic sensor.

The apparatus main body 310 is an apparatus that generates ultrasonic images based on the reflected wave received by the ultrasound probe 320. As illustrated in FIG. 3, the apparatus main body 310 includes a transmitting and receiving unit 311, a B-mode processing unit 312, a Doppler processing unit 313, an image generating unit 314, an image memory 315, a control unit 316, an internal storage unit 317, an interface unit 318, and a volume data processing unit 319.

The transmitting and receiving unit 311 includes a trigger generating circuit, a delay circuit, and a pulser circuit, and supplies driving signals to the ultrasound probe 320. The pulser circuit repeatedly generates rate pulses for forming ultrasonic waves to be transmitted at a predetermined rate frequency. The delay circuit supplies a delay time necessary to converge the ultrasonic waves generated from the ultrasound probe 320 into a beam for each of the piezoelectric transducer elements and to determine the transmission directionality, to each of rate pulses generated by the pulser circuit. The trigger generating circuit applies driving pulses to the ultrasound probe 320 at a timing based on the rate pulses. That is, the delay circuit changes the delay time supplied to each of the rate pulses, thereby arbitrarily adjusting the transmission direction from the surface of the piezoelectric transducer elements.

The transmitting and receiving unit 311 includes an amplifier circuit, an A/D converter, and an adder. The transmitting and receiving unit 311 performs various types of processing on the reflected wave signals received by the ultrasound probe 320 and generates reflected wave data. The amplifier circuit amplifies the reflected wave signals for each channel and performs gain correction processing. The A/D converter supplies a delay time necessary to perform A/D-conversion on the reflected wave signals on which gain correction has been performed and to determine transmission directionality. The adder performs addition processing on the reflected wave signals processed by the A/D converter, thereby generating the reflected wave data. The addition processing performed by the adder enhances a reflect component from the direction corresponding to the reception directionality of the reflected wave signals.

As described above, the transmitting and receiving unit 311 controls the transmission directivity and the reception directionality in transmitting and receiving ultrasound. The transmitting and receiving unit 311 has a function capable of instantly change delay information, a transmission frequency, a transmission drive voltage, the number of aperture elements under the control of the control unit 316, which will be described later. In particular, changes in the transmission drive voltage can be achieved with, a linear amplifier oscillation circuit capable of instantly changing a value, or a mechanism for electrically changing a plurality of power units. The transmitting and receiving unit 311 is capable of transmitting and receiving different waveforms for each frame or each rate.

The B-mode processing unit 312 receives from the transmitting and receiving unit 311, the reflected wave data that is the processed reflected wave signals on which gain correction processing, A/D conversion processing, and addition processing have been performed. The B-mode processing unit 312 then performs logarithm amplification and envelope detection processing, for example, on the received data, thereby generating data in which the signal intensity is represented with the level of brightness (B-mode data).

The Doppler processing unit 313 performs frequency analysis of the speed information using the reflected wave data received from the transmitting and receiving unit 311. The Doppler processing unit 313 then extracts a bloodstream echo component, a tissue echo component, and a contrast material echo component due to the Doppler effect and generates data in which the moving object information such as the average speed, distribution, and power is extracted at multiple points (Doppler data).

The image generating unit 314 generates ultrasonic images from the B-mode data generated by the B-mode processing unit 312 and the Doppler data generated by the Doppler processing unit 313. Specifically, the image generating unit 314 converts scanning line signal arrays of the ultrasound scanning into scanning line signal arrays in a video format typically used in televisions (scan conversion), thereby generating ultrasonic images (e.g., B-mode images and Doppler images) from the B-mode data and the Doppler data.

The image memory 315 stores therein image data such as an enhanced image and a tissue image generated by the image generating unit 314, which will be described later. The image memory 315 also stores therein the processing results by the image generating unit 314. The image memory 315 also stores therein output signals just passed through the transmitting and receiving unit 311, (radio frequency, RF), the brightness signals of the images, various types of raw data, and image data acquired through a network as necessary. The data format of the image data stored in the image memory 315 may be the data format after being converted into the video format to be displayed on the monitor 340 by the control unit 316, which will be described later. The data format of the image data stored in the image memory 315 may also be the data format before being converted into coordinates, which is raw data generated by the B-mode processing unit 312 and the Doppler processing unit 313.

The control unit 316 controls the overall processing performed on the ultrasound diagnosis apparatus 300. Specifically, the control unit 316 controls various types of processing performed by the transmitting and receiving unit 311, the B-mode processing unit 312, the Doppler processing unit 313, and the image generating unit 314 based on various types of setting demands input by an operator through the input device 330, various types of control programs and various types of setting information retrieved from the internal storage unit 317. The control unit 316 also controls the monitor 340 to display thereon the ultrasonic images stored in the image memory 315. The control unit 316 transmits and receives three-dimensional image data (volume data) acquired by other modalities (e.g., an X-ray CT apparatus, an MRI apparatus) through a network according to the digital imaging and communications in medicine (DICOM) standard, for example.

The internal storage unit 317 stores therein control programs for transmitting and receiving the ultrasonic wave, and for image processing and display processing, and various types of data such as diagnosis information (e.g., patient IDs, observations by a doctor) and a diagnosis protocol. The internal storage unit 317 is also used for storing the images stored in the image memory 315 as necessary.

The interface unit 318 is an interface that controls exchanging various types of information between the input device 330, a control device 353, and the apparatus main body 310. The interface unit 318 controls transfer of the positional information acquired by the control device 353 to the control unit 316.

The volume data processing unit 319 executes various types of processing relating to strain analysis. Specifically, through a 3D wall motion tracking technology, an image is generated in which excitation propagation in the heart is drawn. The ultrasound diagnosis apparatus 300 according to the first embodiment here firstly generates the volume data of the heart of the subject P. For example, the ultrasound diagnosis apparatus 300 according to the first embodiment generates a plurality of pieces of volume data (a volume data group) by scanning the left ventricle (LV) of the heart of the subject P along time series during a period of one or more heartbeats.

The volume data processing unit 319 generates motion information on the motion of the core wall, from each piece of the volume data group along time series generated by scanning the heart of the subject P three-dimensionally with the ultrasound. Specifically, the volume data processing unit 319 generates motion information by pattern matching between the pieces of the volume data. More specifically, the volume data processing unit 319 tracks the tracking points that have been set in a cardiac muscle tissue drawn in each piece of the volume data based on speckle patterns, thereby calculating motion vectors of the respective tracking points. The volume data processing unit 319 then uses the motion vectors of the respective tracking points, thereby generating motion information that represents the motion of a local cardiac muscle. In other words, the volume data processing unit 319 performs three-dimensional speckle tracking and generates motion information. For example, the volume data processing unit 319 generates the local area change rate in the cardiac tissue as motion information.

Figure 4:
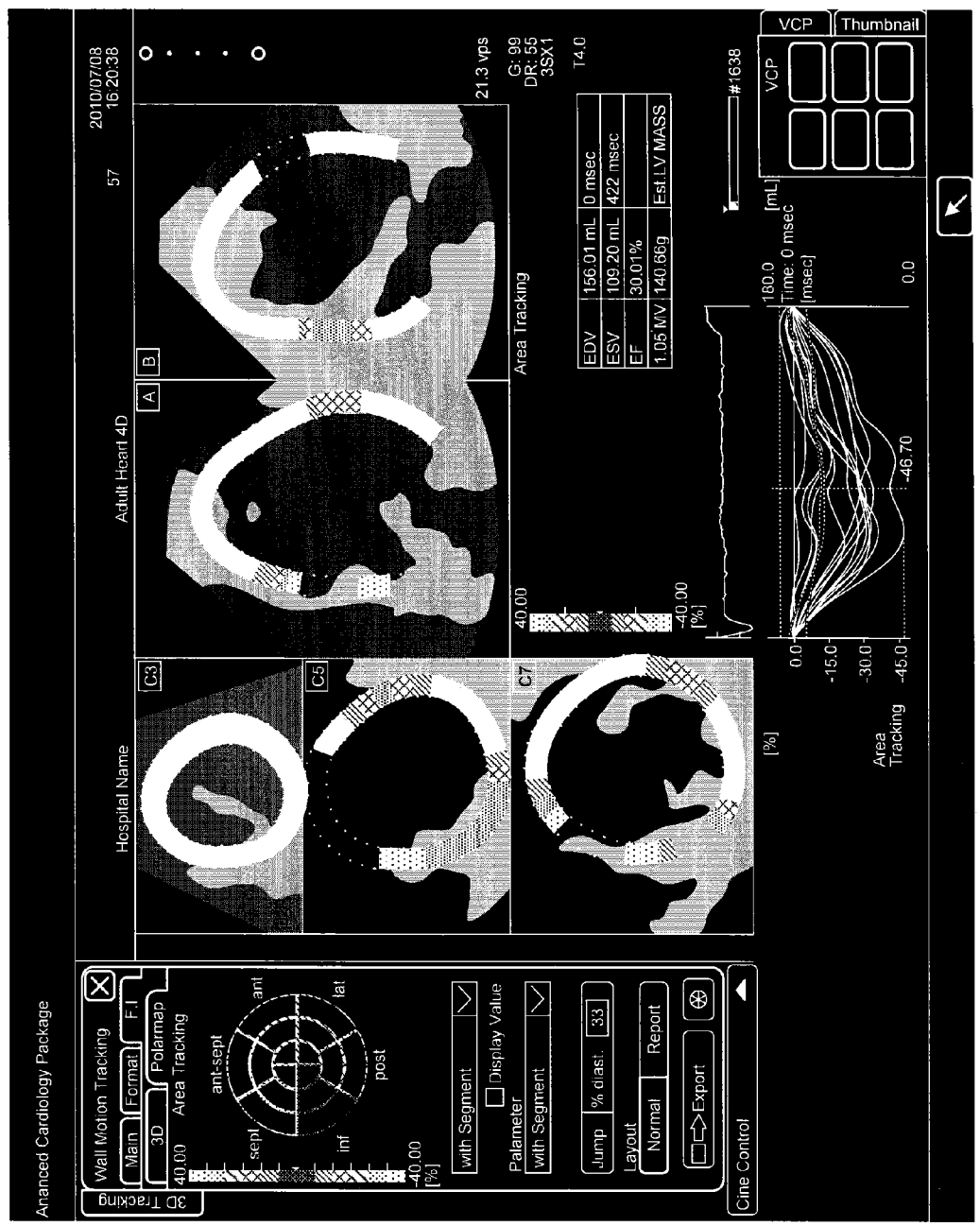
FIG. 4 is a diagram illustrating an example of processing results obtained by a volume data processing unit according to the first embodiment.

FIG. 4 is a diagram illustrating an example of processing results obtained by the volume data processing unit 319 according to the first embodiment. For example, the volume data processing unit 319 can generate a superimposed image in which a specific area is superimposed onto a polar map image through a "time phase holding display method" as illustrated on the left side of FIG. 4. In FIG. 4, "ant-sept" refers to "anteroseptal", "ant" refers to an anterior wall, "lat" refers to a lateral wall, "post" refers to a posterior wall, "inf" refers to an inferior wall, and "sept" refers to "septum".

The volume data processing unit 319 can compose an image from an electrocardiogram and a graph of time change curves of the average motion information (average changing rate of area) for 16 fractions in addition to the time phase holding superimposed image, as illustrated on the bottom in FIG. 4. In FIG. 4, time change curves of the average changing rate of area for each of the 16 fractions are represented with solid lines. Actually, however, the volume data processing unit 319 colors the respective time change curves of the average motion information for each of the 16 fractions in respective colors allocated to each fraction so that it can be understood which time change curve of the average motion information corresponds to which fractions.

The volume data processing unit 319 also generates a plurality of MPR images with a cross section having a short axis or with a cross section having a longitudinal axis from the volume data. In the example illustrated in FIG. 4, the volume data processing unit 319 generates a composite image in the area A. In composite image, a superimposed image including images of a specific area superimposed through the time phase holding method is disposed on the left ventricular core-wall in an apical four-chamber image. In addition, in the example illustrated in FIG. 4, the volume data processing unit 319 generates a composite image in the area B. In composite image, a superimposed image including images of a specific area superimposed through the time phase holding method is disposed on the left ventricular core-wall in an apical two-chamber image.

Furthermore, in the example illustrated in FIG. 4, the volume data processing unit 319 generates a composite image in the area C3. In composite image, a superimposed image including images of a specific area superimposed through the time phase holding method is disposed on the left ventricular core-wall in the image with a cross section having a short axis in the vicinity of the apex. Still furthermore, in the example illustrated in FIG. 4, the volume data processing unit 319 generates a composite image in the area CS. In composite image, a superimposed image including images of a specific area superimposed through the time phase holding method is disposed on the left ventricular core-wall of an image with a cross section having a short axis located between the apex and the base. Still furthermore, in the example illustrated in FIG. 4, the volume data processing unit 319 generates a composite image in the area C7. In the composite image, a superimposed image including images of a specific area superimposed through the time phase holding method is disposed on the left ventricular core-wall in the image with a cross section having a short axis in the vicinity of the base.

In the example illustrated in FIG. 4, together with a color bar and the electrocardiogram, values of various types of motion information are provided as a tabletop. The EDV illustrated in FIG. 4 refers to the volume of the cardiac lumen in the time phase of an end diastole (ED). In the example illustrated in FIG. 4, the EDV indicates "156.01 mL" and the time of the end diastole (reference time phase) indicates "0 msec". The ESV illustrated in FIG. 4 refers to the volume of the cardiac lumen in the time phase of an end systole (ES). In the example illustrated in FIG. 4, the ESV indicates "109.20 mL" and the time of the end systole indicates "422 msec".

The EF illustrated in FIG. 4 refers to the ejection fraction determined from the EDV and the ESV. In the example illustrated in FIG. 4, the EF indicates "30.01%". "1.05×MV" illustrated in FIG. 4 refers to the "cardiac mass (g)" obtained by multiplying the cardiac muscle volume (MV) by the average value of the density of cardiac muscle "1.05 g/mL". In the example illustrated in FIG. 4, "1.05×MV" indicates "140.66 g". Furthermore, in the example illustrated in FIG. 4, "est.LV MASS" is represented, which indicates that the value "140.66 g" is estimated from the cardiac muscle volume of the left ventricle.

Figure 5A:
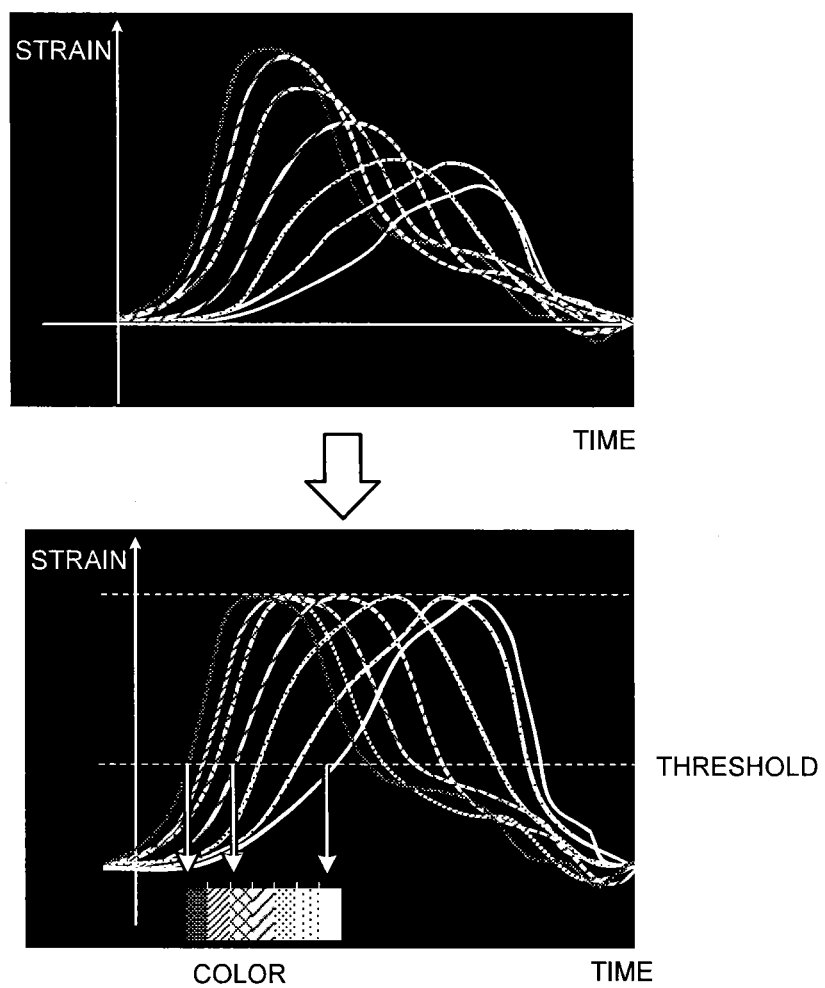
FIG. 5A is a diagram illustrating an example of processing performed by the volume data processing unit according to the first embodiment.

The volume data processing unit 319 may calculate the time change rate (referred to as an "area change rate") of the change in a local area (referred to as a "local area change") as the motion information. That is, the volume data processing unit 319 may calculate the area change rate of the changing rate of area by estimating the time differential value of the local area change. On this occasion, the volume data processing unit 319 changes the color tones of the superimposed image as illustrated in FIG. 5A, by allocating a color for each predetermined threshold time. FIG. 5A is a diagram for explaining an example of processing performed by the volume data processing unit 319 according to the first embodiment.

Figure 5B:
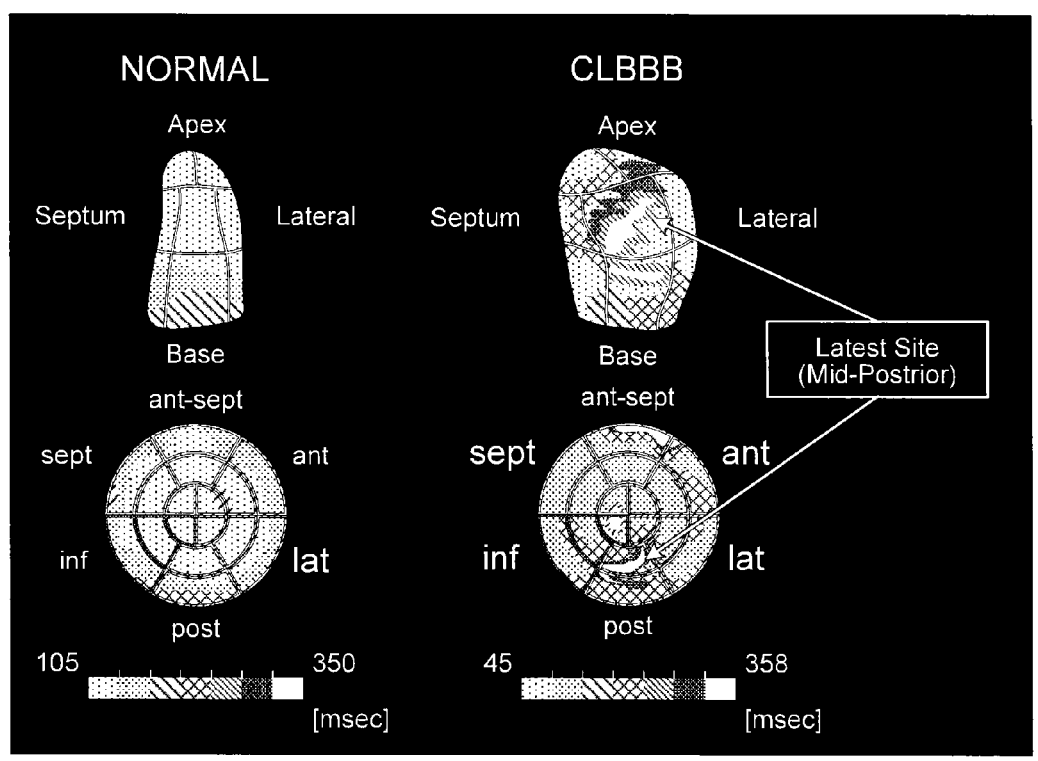
FIG. 5B is a diagram illustrating an example of images generated by the volume data processing unit according to the first embodiment.

FIG. 5B is a diagram illustrating an example of images generated by the volume data processing unit 319 according to the first embodiment. FIG. 5B illustrates the images in which some aspects of excitation propagation in the heart are drawn. Specifically, two following types of superimposed images are illustrated for both an aspect of normal (NORMAL) and an aspect of complete left bundle branch block (CLBBB) in FIG. 5B: the superimposed image color tones are superimposed onto the surface rendering images; and the superimposed image color tones are superimposed onto the polar map images. In the images for CLBBB, sites of latest activation are represented.

In the CRT, the site of latest activation is determined from the superimposed image as illustrated in FIG. 5B, an electrode (a pacing lead) is placed on the closest vein to the site of latest activation, with reference to an X-ray image obtained by using a contrast material. On this occasion, however, the position of the site of latest activation is not accurately represented in the X-ray image. A doctor may therefore perform manipulation trusting his/her own intuition, resulting in placing the electrode in a wrong position. To avoid this, in the image processing apparatus 100 according to the embodiment, by superimposing a superimposed ultrasound image onto the site of latest activation in an X-ray image and displaying the image, an electrode can be placed correctly and the registration of the images can be automated.

Figure 6:
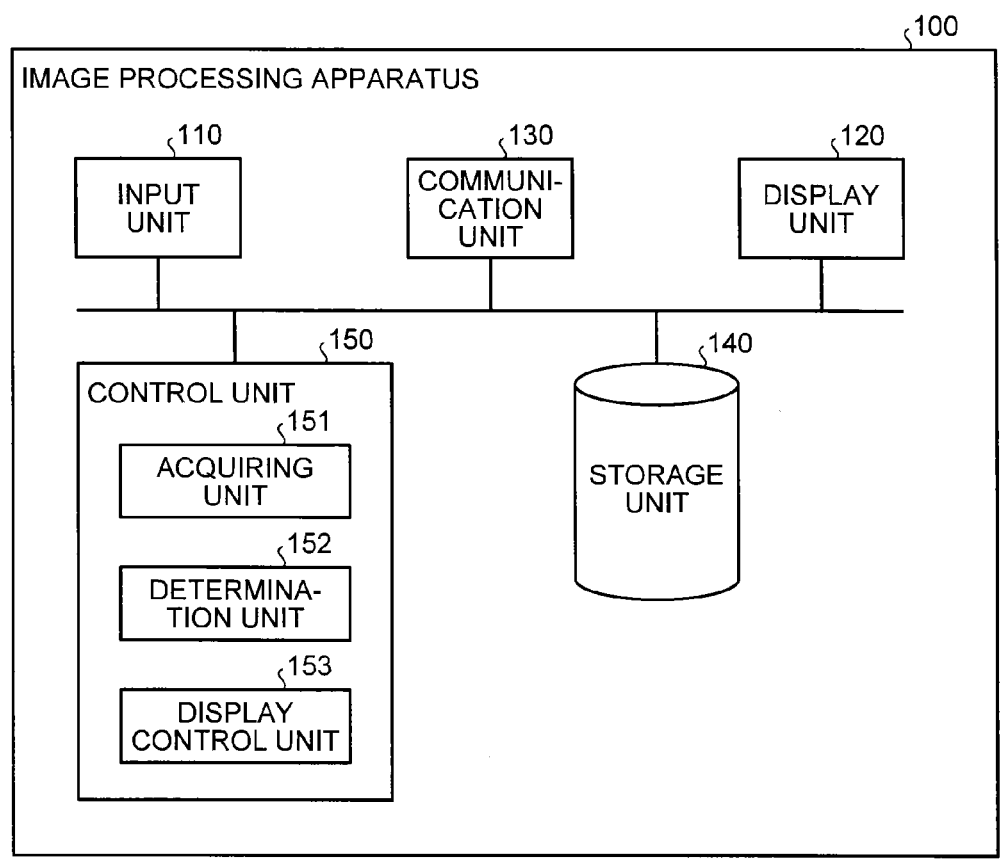
FIG. 6 is a diagram illustrating an example of the configuration of an image processing apparatus according to the first embodiment.

FIG. 6 is a diagram illustrating an example of the configuration of the image processing apparatus 100 according to the first embodiment. As illustrated in FIG. 6, the image processing apparatus 100 includes an input unit 110, a display unit 120, a communication unit 130, a storage unit 140, and a control unit 150. For example, the image processing apparatus 100 is a workstation or a personal computer. The image processing apparatus 100 is coupled to the X-ray diagnosis apparatus 200, the ultrasound diagnosis apparatus 300, and the image storage device 400 through a network.

The input unit 110 is a mouse, a keyboard, or a trackball and receives inputs of various types of operations from an operator (e.g., an interpretation doctor) to the image processing apparatus 100. Specifically, the input unit 110 receives an input of information for acquiring an X-ray image or an ultrasonic image, for example. The input unit 110 receives from an operator (e.g., a surgeon) various types of operations relating to the registration of an X-ray image with an ultrasonic image, for example.

The display unit 120 is a liquid crystal panel as a monitor, for example, and displays various types of information. Specifically, the display unit 120 displays a graphical user interface (GUI) used for receiving various types of operations from the operator and a superimposed image of the X-ray image and the ultrasonic image that are processing results performed by the control unit 150, which will be described later. The communication unit 130 is a network interface card (NIC), for example, and communicates with another device.

The storage unit 140 is, for example, a semiconductor memory device such as a random access memory (RAM) and a flash memory, or a storage device such as a hard disc and an optical disc. The storage unit 140 stores therein X-ray images and ultrasonic images, for example.

The control unit 150 is, for example, an electronic circuit such as a central processing unit (CPU) and a micro processing unit (MPU), or an integrated circuit such as an application specific integrated circuit (ASIC) and a field programmable gate array (FPGA) and controls the image processing apparatus 100 overall.

As illustrated in FIG. 6, the control unit 150 includes an acquiring unit 151, a determination unit 152, and a display control unit 153, for example. The acquiring unit 151 acquires information of the relative position between a radiographic space where the subject P is radiographed by the X-ray diagnosis apparatus 200 and a scanning space where the subject P is scanned by the ultrasound probe 320. Specifically, the acquiring unit 151 acquires the relative positional information according to the positional information of a certain object radiographed by the X-ray diagnosis apparatus 200 and imaged in the X-ray image, or scanned by the ultrasound probe 320 and imaged in the ultrasonic image, and the positional information of the ultrasound probe 320 in the scanning space. More specifically, the acquiring unit 151 acquires the relative positional information according to an X-ray image of the ultrasound probe 320 mounted on the table unit of the X-ray diagnosis apparatus 200 and radiographed from one direction, and the positional information of the ultrasound probe 320 in the scanning space.

Figure 7A:
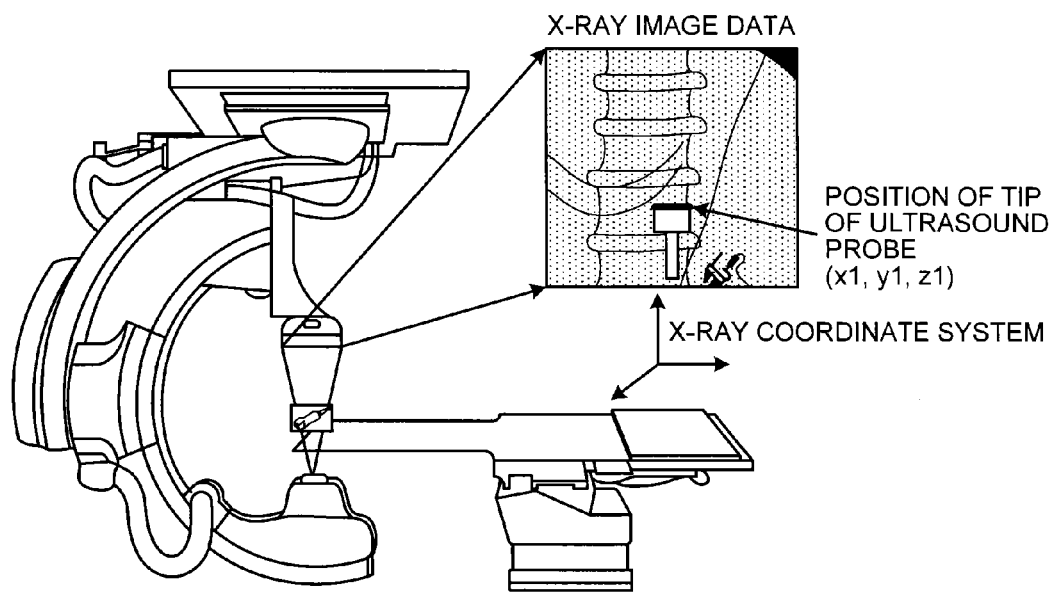
FIG. 7A is a diagram for explaining an example of processing performed by an acquiring unit according to the first embodiment.

FIG. 7A is a diagram for explaining an example of processing performed by the acquiring unit 151 according to the first embodiment. FIG. 7A illustrates radiography of the ultrasound probe 320 by the X-ray diagnosis apparatus 200. For example, as illustrated in FIG. 7A, the acquiring unit 151 acquires an X-ray image of the ultrasound probe 320 mounted on the table unit of the X-ray diagnosis apparatus 200 and radiographed from one direction, and information of the radiographing conditions at that time. Specifically, the acquiring unit 151 acquires the radiographing conditions including the running position on the ceiling of the supporting device of the arm, the height of the table unit, the distance between the X-ray source and the image reception area (source-image distance, SID), and the size of the field of view (FOV) at the time point when the ultrasound probe 320 is radiographed.

The acquiring unit 151 acquires the positional information of the ultrasound probe 320 (coordinates) in the radiographic space of the X-ray image according to the position of the ultrasound probe 320 imaged in the acquired X-ray image and the radiographing conditions. Hereinafter, the coordinates in the radiographic space of the X-ray image is referred to as an X-ray coordinate system. For example, as illustrated in FIG. 7A, the acquiring unit 151 acquires the coordinates (x1, y1, z1) of the tip position of the ultrasound probe 320 in the X-ray coordinate system. For example, the acquiring unit 151 extracts piezoelectric transducer elements and a circuit board imaged in the X-ray image through pattern matching. The acquiring unit 151 then acquires the coordinates (x1, y1, z1) of the tip position of the ultrasound probe 320 based on the extracted parts.

The acquiring unit 151 acquires the coordinates in the ultrasound coordinate system corresponding to the position where the X-ray image is radiographed. That is, the acquiring unit 151 acquires the coordinates (x2, y2, z2) acquired by the position sensor 352 at the position where the X-ray image is radiographed. This enables the acquiring unit 151 to acquire the positional information of the X-ray coordinate system and the corresponding positional information of the ultrasound coordinate system (the relative positional information).

Figure 7B:
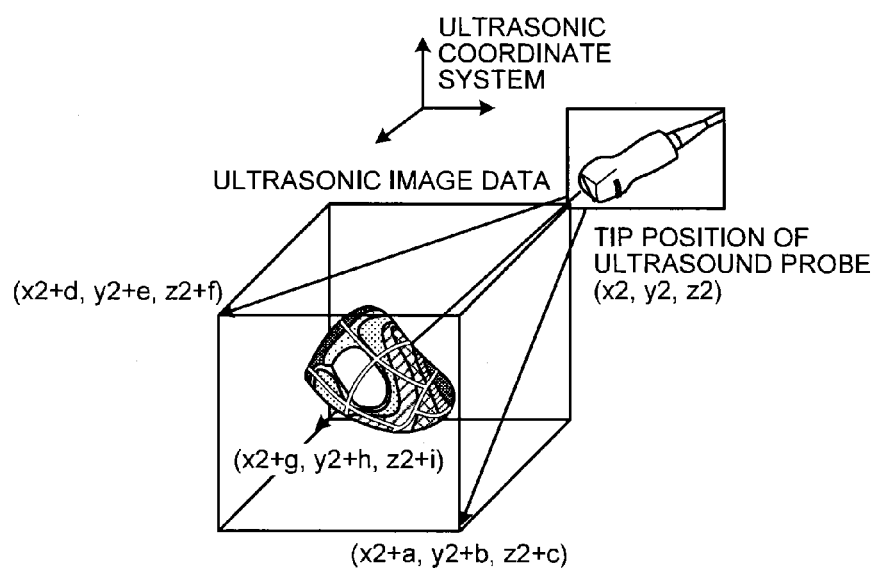
FIG. 7B is a diagram for explaining an example of processing performed by a determination unit according to the first embodiment.
Figure 7C:
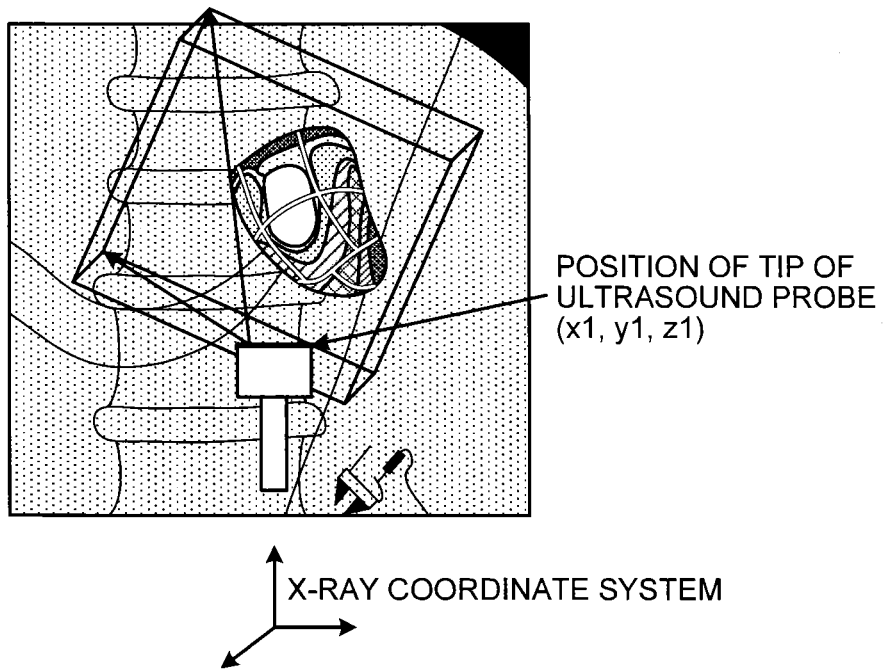
FIG. 7C is a diagram for explaining an example of processing performed by a determination unit according to the first embodiment.

With reference to FIG. 6 again, the determination unit 152 determines the position almost the same as the position scanned by the ultrasound probe 320 in the radiographic space, according to the relative positional information acquired by the acquiring unit 151. FIGS. 7B and 7C are diagrams for explaining examples of processing performed by the determination unit 152 according to the first embodiment. For example, as illustrated in FIG. 7B, the determination unit 152 calculates the coordinates in the scanning region of the ultrasound probe 320 at the time point when the position of the site of latest activation is determined by the ultrasound probe 320 as the coordinates (x2+a, y2+b, z2+c), (x2+d, y2+e, z2+f), (x2+g, y2+h, z2+i) based on the coordinates (x2, y2, z2) of the tip of the ultrasound probe 320 in the ultrasound coordinate system. The determination unit 152 also calculates other apexes in the same manner.

The determination unit 152 calculates the respective calculated coordinates, as illustrated in FIG. 7C, based on the coordinates (x1, y1, z1) of the original position of the tip of the ultrasound probe 320 in the X-ray coordinate system. That is, the determination unit 152 calculates a transformation coefficient based on the coordinates (x2, y2, z2) of the tip in the ultrasound coordinate system and the coordinates (x1, y1, z1) of the tip in the X-ray coordinate system. The determination unit 152 multiplies the respective coordinates when the position of the site of latest activation is determined by the calculated transformation coefficient, thereby determining the position of the site of latest activation in the X-ray coordinate system. On this occasion, the determination unit 152 also calculates the rotation angle and the magnification.

With reference to FIG. 6 again, the display control unit 153 controls the display unit 120 to display thereon a superimposed image in which an image of the target for the scan on the position scanned by the ultrasound probe 320 is superimposed onto the position almost the same as the position determined by the determination unit 152 in an X-ray image radiographed by the X-ray diagnosis apparatus 200. Specifically, the display control unit 153 further superimposes a superimposed image in which the site of latest activation is represented in a different color tone generated by the ultrasound diagnosis apparatus 300 onto the position determined by the determination unit 152 in the X-ray image referred to by a doctor for placing an electrode, and controls the display unit 120 to display thereon the obtained superimposed image.

Figure 8:
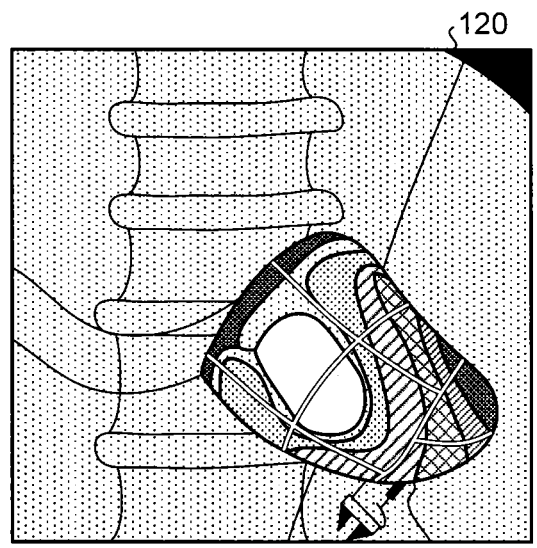
FIG. 8 is a diagram illustrating an example of a display image displayed under control of a display control unit according to the first embodiment.

FIG. 8 is a diagram illustrating an example of display images displayed under control of the display control unit 153 according to the first embodiment. For example, as illustrated in FIG. 8, the display control unit 153 controls the display unit 120 to display thereon a display image in which the ultrasonic image indicating the position of the site of latest activation is superimposed onto the X-ray image. This enables a doctor to recognize the correct position of the site of latest activation in the X-ray image, thereby placing an electrode onto the correct position.

In the above-described example, when acquiring the positional information of the ultrasound probe 320 in the X-ray coordinate system, the ultrasound probe 320 is radiographed from one direction and the positional information (the information of coordinates on three axes, X, Y, and Z) is acquired based on the radiographed image of the ultrasound probe 320 and radiographing conditions. The embodiment, however, is not limited to this example, and various types of embodiments can be achieved.

For example, the ultrasound probe 320 may be radiographed from two directions. In this example, the acquiring unit 151 acquires the relative positional information based on the X-ray image of the ultrasound probe 320 radiographed from two directions by the X-ray diagnosis apparatus 200, and the positional information of the ultrasound probe 320 in the scanning space. Specifically, the acquiring unit 151 acquires the coordinates on three axes, X, Y, and Z from two X-ray images. That is, the acquiring unit 151 calculates the coordinates on the third axis by using the information of the coordinates on two axes obtained from the two images. For example, the acquiring unit may also calculate the height of the table unit by radiographing the ultrasound probe 320 from two directions by the X-ray diagnosis apparatus 200.

For example, the acquiring unit may acquire the volume data of the ultrasound probe 320, and acquire the information of coordinates on the three axes, X, Y, and Z of the ultrasound probe 320 from the acquired volume data. In this example, the acquiring unit 151 acquires the relative positional information based on the three-dimensional data of the ultrasound probe 320 radiographed from multiple directions by the X-ray diagnosis apparatus 200 and the positional information of the ultrasound probe 320 in the scanning space.

For another example, a certain object (material) that can be scanned by the ultrasound probe 320 may be embedded in the table unit. In this example, the acquiring unit 151 acquires the relative positional information based on the object that can be scanned by the ultrasound probe 320, and provided in advance in a predetermined position on the table unit of the X-ray diagnosis apparatus 200 and the positional information of the ultrasound probe 320 in the scanning space. That is, the acquiring unit 151 performs registration by using the coordinates in the X-ray coordinate system of the position where the object that can be scanned is provided, and the ultrasound coordinate system when the object is scanned.

The following describes procedures of processing performed by the image processing apparatus 100 according to the first embodiment. FIG. 9 is a flowchart illustrating procedures of processing performed by the image processing apparatus 100 according to the first embodiment. The flowchart illustrated in FIG. 9 includes processing performed by the X-ray diagnosis apparatus 200 and processing performed by the ultrasound diagnosis apparatus 300 in addition to processing performed by the image processing apparatus 100.

As illustrated in FIG. 9, in the image processing apparatus 100 according to the first embodiment, the X-ray diagnosis apparatus 200 acquires an X-ray image of the ultrasound probe 320 (Step S101). The acquiring unit 151 then determines the coordinates of the tip of the ultrasound probe 320 in the X-ray coordinate system (Step S102).

The acquiring unit 151 subsequently determines the coordinates of the tip of the ultrasound probe 320 in the ultrasound coordinate system (Step S103). After that, in the ultrasound diagnosis apparatus 300, ultrasonic images are acquired for determining the position of the site of latest activation (Step S104), and the site of latest activation is determined.

Subsequently, the determination unit 152 determines the coordinates of the site of interest (the site of latest activation) in the ultrasound coordinate system (Step S105). After that, the determination unit 152 calculates a transformation coefficient from the coordinates of the ultrasound probe 320 in the X-ray coordinate system and the coordinates of the ultrasound probe 320 in the ultrasound coordinate system (Step S106).

Subsequently, the determination unit 152 transforms the coordinates of the site of interest (the site of latest activation) in the ultrasound coordinate system into the coordinates in the X-ray coordinate system by using the calculated transformation coefficient (Step S107). After that, the display control unit 153 displays superimposed image in which the ultrasonic image illustrating the site of latest activation is superimposed onto the position of the site of latest activation in the X-ray image (Step S108), and the processing ends.

With reference to FIG. 9, procedures of processing performed by the image processing apparatus 100 according to the first embodiment have been described. The following describes the workflow of a surgeon using the image processing apparatus 100 in this application, with reference to FIG. 10. That is, FIG. 10 includes processing performed by the surgeon, processing performed by the image processing apparatus 100 in response to an operation input by the surgeon through the input unit 110, processing performed by the X-ray diagnosis apparatus 200 in response to an operation by the surgeon, and processing performed by ultrasound diagnosis apparatus 300 in response to an operation by the surgeon. FIG. 10 is a flowchart illustrating procedures of a surgeon using the image processing apparatus 100 according to the first embodiment. As preparation for an operation, the surgeon places the ultrasound probe 320 on the table unit of the X-ray diagnosis apparatus 200 (Step S201). The surgeon operates the X-ray diagnosis apparatus 200, thereby acquiring the X-ray images of the ultrasound probe 320 placed on the table unit (Step S202).

The surgeon then operates the image processing apparatus 100, thereby determining the position "i", the tip of the ultrasound probe 320 in the X-ray coordinate system by using the acquired X-ray images (Step S203). This enables the surgeon to locate the position of the ultrasound probe 320 in the X-ray coordinate system where the X-ray image is radiographed (i.e., the X-ray coordinate system can be associated with the ultrasound coordinate system). As described above, the surgeon determines in advance the position of the ultrasound probe 320 in the X-ray coordinate system at the stage of preparation before the surgery.

Subsequently, at the stage of determining the treatment, the subject enters the room and lies down on the table unit of the X-ray diagnosis apparatus (Step S204). The surgeon scans the subject by using the ultrasound probe 320 and acquires images of the site of lesion (Step S205). The surgeon then operates the ultrasound diagnosis apparatus 300, thereby determining "ii", the position of the ultrasonic image in the ultrasound coordinate system (Step S206), and "iii", the position of the tip of the ultrasound probe 320 in the ultrasound coordinate system (Step S207). The surgeon operates the image processing apparatus 100 to compare the position "i" determined at the stage of preparation before the surgery to the position "iii", and calculate a transformation coefficient for transforming the position "ii" in the ultrasonic image of the site of lesion into the X-ray coordinate system (Step S208). This achieves registration of the position in the ultrasonic image with the position in the X-ray image.

At the stage of treatment, the image processing apparatus 100 rotates and enlarges the ultrasonic image according to the transformation coefficient, superimposes the image onto the X-ray image, and displays them (Step S209). The surgeon treats the site of lesion while watching the displayed X-ray image (+the ultrasonic image) (Step S210). After the manipulation is completed, the subject leaves the room and the treatment ends (Step S211).

As described above, according to the first embodiment, the acquiring unit 151 acquires the relative positional information between the radiographic space where the subject P is radiographed by the X-ray diagnosis apparatus 200 and, the scanning space where the subject P is scanned using the ultrasound probe 320. The determination unit 152 then determines the position almost the same as the position scanned by the ultrasound probe 320 in the radiographic space based on the relative positional information acquired by the acquiring unit 151. The acquiring unit 151 acquires the relative positional information based on the X-ray image radiographed by the X-ray diagnosis apparatus 200. This enables the image processing apparatus 100 according to the first embodiment to automatically determine the site of latest activation in the X-ray image in a precise manner. This achieves readily acquiring the correct positional information of the site of latest activation in the X-ray image. As a result, the image processing apparatus 100 achieves placing an electrode in a precise manner.

According to the first embodiment, the acquiring unit 151 acquires the relative positional information according to the positional information of the object radiographed by the X-ray diagnosis apparatus 200 and imaged in the X-ray image or scanned by the ultrasound probe 320 and imaged in the ultrasonic image, and the positional information of the scanning space. The image processing apparatus 100 according to the first embodiment, therefore, achieves automatic registration simply by radiographing, thereby readily acquiring the correct positional information of the site of latest activation in the X-ray image without bothering operators.

According to the first embodiment, the acquiring unit 151 acquires the relative positional information according to an X-ray image of the ultrasound probe 320 mounted on the table unit of the X-ray diagnosis apparatus 200 and radiographed from one direction, information on the height of the table unit included in the X-ray diagnosis apparatus 200, and the positional information of the ultrasound probe 320 in the scanning space. This enables the image processing apparatus 100 according to the first embodiment to readily acquire the relative position.

According to the first embodiment, the acquiring unit 151 acquires the relative positional information based on the X-ray image of the ultrasound probe radiographed from two directions by the X-ray diagnosis apparatus 200, and the positional information of the ultrasound probe 320 in the scanning space. This enables the image processing apparatus 100 according to the first embodiment to readily acquire the relative position without limiting the position of the ultrasound probe 320 to a position on the table unit.

According to the first embodiment, the acquiring unit 151 acquires the relative positional information based on the three-dimensional data of the ultrasound probe 320 radiographed from multiple directions by the X-ray diagnosis apparatus 200, and the positional information of the ultrasound probe 320 in the scanning space. The three-dimensional data is generated based on the image data acquired from the X-ray diagnosis apparatus 200 so as to have enough amount of information for transforming the position of the ultrasound probe in the three-dimensional data into the X-ray coordinate system. This enables the image processing apparatus 100 according to the first embodiment to acquire more detailed positional information.

According to the first embodiment, the acquiring unit 151 acquires the relative positional information based on the object that can be scanned by the ultrasound probe 320 provided in advance in a predetermined position on the table unit of the X-ray diagnosis apparatus 200 and the positional information of the ultrasound probe 320 in the scanning space. This enables the image processing apparatus 100 according to the first embodiment to acquire the relative positional information by scanning to a small extent in addition to the scan for determining the site of latest activation using the ultrasound probe 320 without radiographing in advance.

In addition to the first embodiment described above, different embodiments may be achieved.

In the above-described first embodiment, the X-ray coordinate system is associated with the ultrasound coordinate system by using the X-ray image of the ultrasound probe 320 or the ultrasonic image of an object (material) on the table unit. The embodiment, however, is not limited to this example. For another example, a position sensor may be used. In this example, a position sensor is firstly provided in a predetermined position of the X-ray diagnosis apparatus 200. The position of the position sensor is within a magnetic field generated by the transmitter 351 and preferably away from any part made of a metal.

That is, the positional information acquired by the additionally provided position sensor and transmitted to the control device 353 is of already-known coordinates in the X-ray coordinate system. The determination unit 152 therefore calculates a transformation coefficient from the coordinates in the ultrasound coordinate system acquired by the additionally provided position sensor and the already-known coordinates in the X-ray coordinate system. The determination unit 152 then determines the position by using the calculated transformation coefficient.

For another example, a jig may be used. In this example, the acquiring unit 151 acquires the relative positional information based on a fixing area for the ultrasound probe 320 provided in a predetermined position of the X-ray diagnosis apparatus 200, and the positional information of the ultrasound probe 320 in the scanning space. The jig here refers to a tool for fixing the ultrasound probe 320.

That is, a fixing area is additionally provided on a predetermined place of the X-ray diagnosis apparatus 200 for fixing the ultrasound probe 320. Before performing registration, the ultrasound probe 320 is fixed on the fixing area and the coordinates of the ultrasound probe 320 in the ultrasound coordinate system at that time is acquired. The determination unit 152 calculates a transformation coefficient from the acquired coordinates and the coordinates of the fixing area. The determination unit 152 determines the position by using the calculated transformation coefficient.

The positional information of the ultrasound probe 320 in the scanning space is determined by the relative positional relation between the control device 353 and the ultrasound probe 320. When using a jig and if the position of the control device 353 is not changed, the coordinates of the ultrasound probe 320 in the ultrasound coordinate system is always the same. Based on this fact, if the position of the control device 353 can be fixed, the coordinates of the ultrasound probe 320 in the ultrasound coordinate system acquired in the past may be used.

In the embodiment described above, the image processing apparatus 100 locates the site of latest activation on the X-ray image and superimposes the ultrasonic image on the located position. The embodiment, however, is not limited to this example. For another example, the above-described image processing apparatus 100 is included in an X-ray diagnosis apparatus 200. That is, a system control unit 221 of the X-ray diagnosis apparatus 200 may include the above-described acquiring unit 151, the determination unit 152, and the display control unit 153 and perform the above-described processing.

According to an image processing apparatus according to at least one of the embodiments described above, the correct positional information of the site of latest activation in the X-ray image can be readily acquired.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
    processing circuitry configured to
        acquire information of a relative position between a radiographic space where a subject is radiographed by an X-ray diagnosis apparatus and a scanning space where the subject is scanned by an ultrasound probe; and
        determine a position almost a same as a position scanned by the ultrasound probe in the radiographic space, according to the information of the acquired relative position, wherein
    the processing circuitry is further configured to
        acquire positional information of the ultrasound probe in the radiographic space based on an X-ray image of the ultrasound probe mounted on a table of the X-ray diagnosis apparatus and radiographed from one direction, and a geometry of the X-ray diagnosis apparatus,
        acquire positional information of the ultrasound probe in the scanning space corresponding to a position where the X-ray image is radiographed, and
        acquire the information of the relative position based on the positional information of the ultrasound probe in the radiographic space and the positional information of the ultrasound probe in the scanning space.

2. The image processing apparatus according to claim 1, wherein the processing circuitry is further configured to acquire the information of the relative position according to a certain object radiographed by the X-ray diagnosis apparatus and imaged in an X-ray image, or scanned by the ultrasound probe and imaged in an ultrasonic image, and the positional information of the ultrasound probe in the scanning space.

3. The image processing apparatus according to claim 1, wherein the processing circuitry is further configured to calculate a height of the table based on an X-ray image of the ultrasound probe radiographed from two directions by the X-ray diagnosis apparatus.

4. The image processing apparatus according to claim 2, wherein the processing circuitry is further configured to acquire the information of the relative position according to three-dimensional data of the ultrasound probe radiographed from multiple directions by the X-ray diagnosis apparatus and the positional information of the ultrasound probe in the scanning space.

5. The image processing apparatus according to claim 2, wherein the processing circuitry is further configured to calculate the information of the relative position based on the object that is capable of being scanned by the ultrasound probe, the object being provided in advance in a predetermined position on the table of the X-ray diagnosis apparatus, and the positional information of the ultrasound probe in the scanning space.

6. The image processing apparatus according to claim 1, wherein the processing circuitry is further configured to acquire the information of the relative position based on a position sensor provided in a predetermined position on the X-ray diagnosis apparatus and a position sensor provided on the ultrasound probe.

7. The image processing apparatus according to claim 1, wherein the processing circuitry is further configured to control a display to display thereon a superimposed image in which an image of the target for the scan on the position scanned by the ultrasound probe is superimposed onto the position almost the same as the determined position in an X-ray image radiographed by the X-ray diagnosis apparatus.

8. The image processing apparatus according to claim 1, wherein the processing circuitry is further configured to acquire the information of the relative position at a stage of preparation before surgery.

9. An X-ray diagnosis apparatus, comprising:
    processing circuitry configured to
        acquire information of a relative position between a radiographic space where a subject is radiographed and a scanning space where the subject is scanned by an ultrasound probe; and
        determine a position almost a same as a position scanned by the ultrasound probe in the radiographic space, according to the information of the acquired relative position, wherein
    the processing circuitry is further configured to
        acquire positional information of the ultrasound probe in the radiographic space based on an X-ray image of the ultrasound probe mounted on a table of the X-ray diagnosis apparatus and radiographed from one direction, and a geometry of the X-ray diagnosis apparatus,
        acquire positional information of the ultrasound probe in the scanning space corresponding to a position where the X-ray image is radiographed, and
        acquire the information of the relative position based on the positional information of the ultrasound probe in the radiographic space and the positional information of the ultrasound probe in the scanning space.

10. A registration method performed by an image processing apparatus, the registration method comprising:
    acquiring information of a relative position between a radiographic space where a subject is radiographed by an X-ray diagnosis apparatus and a scanning space where the subject is scanned by an ultrasound probe; and
    determining a position almost a same as a position scanned by the ultrasound probe in the radiographic space, according to the information of the acquired relative position, wherein
    the information of the relative position is acquired based on positional information of the ultrasound probe in the radiographic space and positional information of the ultrasound probe in the scanning space, wherein
    the positional information of the ultrasound probe in the radiographic space is acquired based on an X-ray image of the ultrasound probe mounted on a table of the X-ray diagnosis apparatus and radiographed from one direction, and a geometry of the X-ray diagnosis apparatus, and the positional information of the ultrasound probe in the scanning space corresponds to a position where the X-ray image is radiographed.

* * * * *